(12) United States Patent
Feng et al.

(10) Patent No.: US 9,574,982 B2
(45) Date of Patent: Feb. 21, 2017

(54) METHOD OF MEASURING CONCENTRATIONS OF GAS MIXTURES

(71) Applicant: Carrier Corporation, Farmington, CT (US)

(72) Inventors: Yinshan Feng, South Windsor, CT (US); Parmesh Verma, South Windsor, CT (US); Mary Teresa Lombardo, Windsor, CT (US)

(73) Assignee: CARRIER CORPORATION, Farmington, CT (US)

( * ) Notice: Subject to any disclaimer, the term of this patent is extended or adjusted under 35 U.S.C. 154(b) by 92 days.

(21) Appl. No.: 14/438,855

(22) PCT Filed: Aug. 23, 2013

(86) PCT No.: PCT/US2013/056449
§ 371 (c)(1),
(2) Date: Apr. 27, 2015

(87) PCT Pub. No.: WO2014/065937
PCT Pub. Date: May 1, 2014

(65) Prior Publication Data
US 2015/0293002 A1 Oct. 15, 2015

Related U.S. Application Data

(60) Provisional application No. 61/718,446, filed on Oct. 25, 2012.

(51) Int. Cl.
*G01N 7/00* (2006.01)
*G01N 25/58* (2006.01)
(Continued)

(52) U.S. Cl.
CPC ............. *G01N 7/00* (2013.01); *G01N 25/58*

(2013.01); *F25B 49/00* (2013.01); *F25B 2400/08* (2013.01); *G01N 7/14* (2013.01)

(58) Field of Classification Search
CPC ............ G01N 7/00; G01N 7/14; G01N 25/58; F25B 49/00; F25B 2400/08
(Continued)

(56) References Cited

U.S. PATENT DOCUMENTS 3,264,862 A * 8/1966 Felton ..................... G01N 25/00
73/25.01
3,535,915 A * 10/1970 Buehler ................ G01N 25/00
73/25.01
(Continued)

FOREIGN PATENT DOCUMENTS

CN 101581650 A 11/2009

OTHER PUBLICATIONS

Non-Patent Literature "Measurement and Prediction of Vapor Pressure of Binary and Ternary Systems Containing 1-Ethyl-3-methlyimidazolium Ethyl Sulfate", Wang, J. F. et al., Journal of Chemical and Engineering Data, vol. 52, No. 4, 2007, pp. 1307-1312.*

(Continued)

*Primary Examiner* — Laura Martin
*Assistant Examiner* — Irving A Campbell
(74) *Attorney, Agent, or Firm* — Cantor Colburn LLP

(57) ABSTRACT

A method of measuring concentrations of gas mixtures is disclosed in which an ionic liquid and/or low vapor-pressure organic solvent is exposed to a gas mixture being tested to form a solution of the gas components in the liquid. The vapor pressure of the solution is then measured at one or more other temperatures and compared to predicted vapor pressures based on known individual vapor pressure profiles of the gas components in the liquid in order to determine the actual proportions of the components in the gas sample.

18 Claims, 4 Drawing Sheets

(51) Int. Cl.
*G01N 7/14* (2006.01)
*F25B 49/00* (2006.01)

(58) Field of Classification Search
USPC .......................................................... 73/25.04
See application file for complete search history.

(56) References Cited

U.S. PATENT DOCUMENTS

| | | | |
|---|---|---|---|
| 3,843,489 | A | 10/1974 | Sandler |
| 4,901,559 | A | 2/1990 | Grabner |
| 5,022,259 | A | 6/1991 | Lee et al. |
| 5,158,747 | A | 10/1992 | Manz et al. |
| 5,186,012 | A | 2/1993 | Czachorski et al. |
| 5,237,873 | A | 8/1993 | Eichenlaub |
| 5,295,360 | A | 3/1994 | Olds et al. |
| 5,392,639 | A * | 2/1995 | Manz .................. G01N 25/00 422/83 |
| 5,410,887 | A | 5/1995 | Urata et al. |
| 5,698,750 | A | 12/1997 | Mouk et al. |
| 5,987,907 | A | 11/1999 | Morimoto et al. |
| 5,996,358 | A | 12/1999 | Sumida et al. |
| 6,035,648 | A | 3/2000 | Hickman et al. |
| 6,076,392 | A * | 6/2000 | Drzewiecki ....... A61M 16/0051 422/83 |
| 6,079,217 | A | 6/2000 | Judge |
| 6,138,497 | A | 10/2000 | Nix et al. |
| 6,458,249 | B2 | 10/2002 | Miller et al. |
| 6,560,981 | B2 | 5/2003 | Flynn |
| 6,823,743 | B2 * | 11/2004 | Sato ...................... G01N 7/00 73/204.11 |
| 7,708,903 | B2 | 5/2010 | Sievert et al. |
| 7,964,760 | B2 | 6/2011 | Shiflett et al. |
| 8,785,711 | B2 * | 7/2014 | Lee ......................... C07C 7/10 585/809 |
| 2004/0133058 | A1 * | 7/2004 | Arlt ......................... B01D 3/40 585/833 |
| 2007/0131535 | A1 | 6/2007 | Shiflett et al. |
| 2011/0000236 | A1 | 1/2011 | Seiler et al. |

OTHER PUBLICATIONS

Non-Patent Literature "Ionic liquids in separations of azeotropic systems—A review", A. B. Pereiro et al., J. Chem. Thermodynamics 46 (2012) 2-28.*

Amir Hossein Jalili et al: "Solubility of CO 2, H 2 S, and Their Mixture in the Ionic Liquid 1-Octyl-3-methylimidazolium Bis (tribluormethyl) sulfonylimide," The Journal of Physical Chemistry B, vol. 116, No. 9, Mar. 8, 2012; pp. 2758-2774.

Notification Concerning Transmittal of International Preliminary Report on Patentability and Written Opinion of the International Searching Authority regarding related International Application No. PCT/US2013/056449; dated Apr. 28, 2015; 10 pages.

Shiflett, Mark and Yokozeki, A., Separation of Carbon Dioxide and Sulfur Dioxide Using Room-Temperature Ionic Liquic [bmim-][MeSO4]; Energy Fuels 2010, 24, 1001-1008; Published on Web Nov. 19, 2009; 8 pgs.

Shiflett, Mark; Yokozeki, A; Solubility and Diffusivity of Hydrofluorocarbons in Room-Temperatrues Ionic Liquids; AIChE Journal; Mar. 2006; 15 pgs.

Zhao, Jin; Jiang, Xiao-Chuan; Li, Chun-Xi; and Wang, Zi-Hao; Vapor pressure measurement for binary and ternary systems containing a phosphoric ionic liquid; Science Direct; Jul. 2006; 9 pgs.

Jalili, Amir Hossein, Safavi, Mohammadali, et al., Solubility of CO2, H2S, and their Mixture in the Ionic Liquid 1-Octyl-3-methylimidazolium Bis (trifluoromethyl)sulfonylimide; The Journal of Physical Chemistry; 2012; pp. 2758-2774.

English translation of Office Action regarding related CN App. No. 201380055802.6, Issued Aug. 23, 2016.

* cited by examiner

METHOD OF MEASURING CONCENTRATIONS OF GAS MIXTURES

CROSS REFERENCE TO RELATED APPLICATIONS

This application is a National Phase Application of Patent Application PCT/US2013/056449 filed on Aug. 23, 2013, which claims priority to U.S. 61/718,446 filed Oct. 25, 2012, the disclosure of which is incorporated herein by reference in its entirety.

BACKGROUND OF THE INVENTION

The subject matter disclosed herein generally relates to methods and apparatus for determining concentrations of gas mixtures.

With modern sophisticated chemical analytical techniques such as gas chromatography—mass spectrometry, it is generally possible to determine the composition of gas mixtures with a relatively high degree of precision. However, such sophisticated techniques can be time consuming and expensive, and simpler, faster, and/or less expensive techniques are often desired. In some situations, the identity of the components in a gas mixture may already be known with reasonable certainty, and it is only necessary to determine the concentrations of the already-identified components of the mixture.

One example of this is with a refrigeration system such as a chiller or air conditioning system having a heat transfer loop with a refrigerant flowing through it. In the past, refrigerants used in heat transfer loops often consisted of a single compound such as R-12, R-22, or R-134a. However, increasing demands for refrigerants that can meet demanding specifications across a number of parameters, such as heat transfer performance, ozone depletion potential (ODP), global warming potential (GWP), toxicity, and/or flammability, have necessitated that blends of different compounds for use as refrigerants in order to provide desired performance. The use of refrigerant blends, however, can lead to problems in monitoring and maintaining refrigeration system performance. For example, refrigeration systems can be prone to developing leaks in the refrigerant loop. With a single-compound refrigerant, a small leak may not have a significant adverse impact on system performance until a substantial quantity of refrigerant has leaked out of the system. With a blended refrigerant, however, a leak can cause fractionation, which alters the composition of the refrigerant blend remaining in the system and can adversely impact refrigerant properties or performance. Therefore, it is desirable to be able to determine the concentration of components in a refrigerant blend.

Attempts have been made to determine refrigerant blend compositions by monitoring the refrigerant state (e.g., temperature and pressure) at different locations in the refrigerant loop. For example, U.S. Pat. No. 6,079,217 discloses a refrigeration system that attempts to determine the composition of a ternary blend of four refrigerants by measuring the refrigerant states (e.g., pressure and temperature) at the inlet and outlet of expansion device, such that the composition of blend can be determined based on the isenthalpic assumption and the vapor-liquid-equilibrium diagram. Such attempts, however, are subject to a number of disadvantages, such as only being useful for non-azeotropic blends, lack of portability, and they require the permanent installation of costly temperature and pressure sensors and control subsystems in each refrigeration system.

BRIEF DESCRIPTION OF THE INVENTION

In an aspect of the invention, a method of measuring the concentration of an identified subject compound in a gaseous mixture comprising the subject compound and at least one other identified compound or compounds comprises:

(a) exposing a liquid comprising an ionic liquid and/or a low vapor-pressure organic solvent to the gaseous mixture at a first temperature and a first pressure until the liquid and the gaseous mixture are in equilibrium, thereby forming a liquid solution comprising the ionic liquid and/or low vapor pressure organic solvent, the subject compound, and the at least one other compound or compounds;

(b) isolating the liquid solution from the gaseous mixture;

(c) determining a predicted vapor pressure function of the liquid solution at a second temperature as a function of the concentration of each of the subject compound and the at least one other identified compound or compounds, wherein the predicted vapor pressure of the liquid solution at a given molar concentration of each of the compounds equals the sum of the vapor pressure of each compound multiplied by its given mole percentage based on total number of moles of the subject compound and the at least one other identified compound or compounds in solution in the liquid;

(d) measuring the vapor pressure of the liquid solution at the second temperature;

(e) comparing the measured vapor pressure of the liquid solution at the second temperature with predicted vapor pressure of the liquid solution at the second temperature and identifying all molar concentration profiles of the identified subject compound and the at least one other identified compound or compounds in the liquid for which the measured vapor pressure equals the predicted vapor pressure;

(f) if more than one molar concentration profile of the identified subject compound and the at least one other identified compound or compounds in the liquid provides a predicted vapor pressure that equals the measured vapor pressure at the second temperature, repeating steps (c)-(e) at different temperatures until a single molar concentration profile provides a predicted vapor pressure that matches the measured vapor pressure at each of the second and additional temperatures;

(g) converting the single concentration profile resulting from step (e) or step (f) by the solubility in the liquid at the first temperature of each of the identified subject compound and the at least one other identified compound or compounds, respectively to a concentration profile of the identified subject compound and the at least one other identified compound or compounds in the liquid resulting from step (a);

(h) calculating a partial vapor pressure for each of the identified subject compound and the at least one other identified compound or compounds in the gaseous mixture by dividing the mole percentage of each of the identified subject compound and the at least one other identified compound or compounds in; and (i) calculating a mole percent of the identified subject compound in the gaseous mixture by dividing the partial vapor pressure of the identified subject compound from step (h) by the sum of the partial vapor pressures for each of the identified subject compound and the at least one other identified compound or compounds from step (h).

In a further aspect of the invention, an apparatus for determining the concentration of an identified subject compound in a gaseous mixture comprises a container having a liquid therein comprising an ionic liquid and/or a low vapor-pressure organic solvent, a temperature sensor for measuring temperature of the liquid in the container, a pressure sensor for measuring vapor pressure of the liquid, and a sample port in interruptible fluid communication with the interior of the container.

In a still further aspect of this invention, the apparatus further comprises a controller configured to (a) open fluid communication between the sample port and the container when the sample port is connected the gaseous mixture to expose the liquid in the container to the gaseous mixture at a first temperature and a first pressure until the liquid and the gaseous mixture are in equilibrium, thereby forming a liquid solution comprising the ionic liquid and/or low vapor pressure organic solvent, the subject compound, and the at least one other compound or compounds;

(b) interrupt fluid communication between sample port and the container to isolate the liquid solution from the gaseous mixture;

(c) determine a predicted vapor pressure function of the liquid solution at a second temperature, which can be the same as or different than the first temperature, as a function of the concentration of each of the subject compound and the at least one other identified compound or compounds, wherein the predicted vapor pressure of the liquid solution at a given molar concentration of each of the compounds equals the sum of the vapor pressure of each compound multiplied by its given mole percentage based on total number of moles of the subject compound and the at least one other identified compound or compounds in solution in the liquid;

(d) record a measured vapor pressure of the liquid solution sensed by the pressure sensor at the second temperature;

(e) compare the measured vapor pressure of the liquid solution at the second temperature with predicted vapor pressure of the liquid solution at the second temperature and identifying all molar concentration profiles of the identified subject compound and the at least one other identified compound or compounds in the liquid for which the measured vapor pressure equals the predicted vapor pressure;

(f) if more than one molar concentration profile of the identified subject compound and the at least one other identified compound or compounds in the liquid provides a predicted vapor pressure that equals the measured vapor pressure at the second temperature, repeat steps (c)-(e) at different temperatures until a single molar concentration profile provides a predicted vapor pressure that matches the measured vapor pressure at each of the second and additional temperatures;

(g) convert the single concentration profile resulting from step (e) or step (f) by the solubility in the liquid at the first temperature of each identified subject compound and the at least one other identified compound or compounds, respectively to a concentration profile of the identified subject compound and the at least one other identified compound or compounds in the liquid resulting from step (a);

(h) calculate a partial vapor pressure for each of the identified subject compound and the at least one other identified compound or compounds in the gaseous mixture by dividing the mole percentage of each of the identified subject compound and the at least one other identified compound or compounds in; and (i) calculate a mole percent of the identified subject compound in the gaseous mixture by dividing the partial vapor pressure of the identified subject compound from step (h) by the sum of the partial vapor pressures for each of the identified subject compound and the at least one other identified compound or compounds from step (h).

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
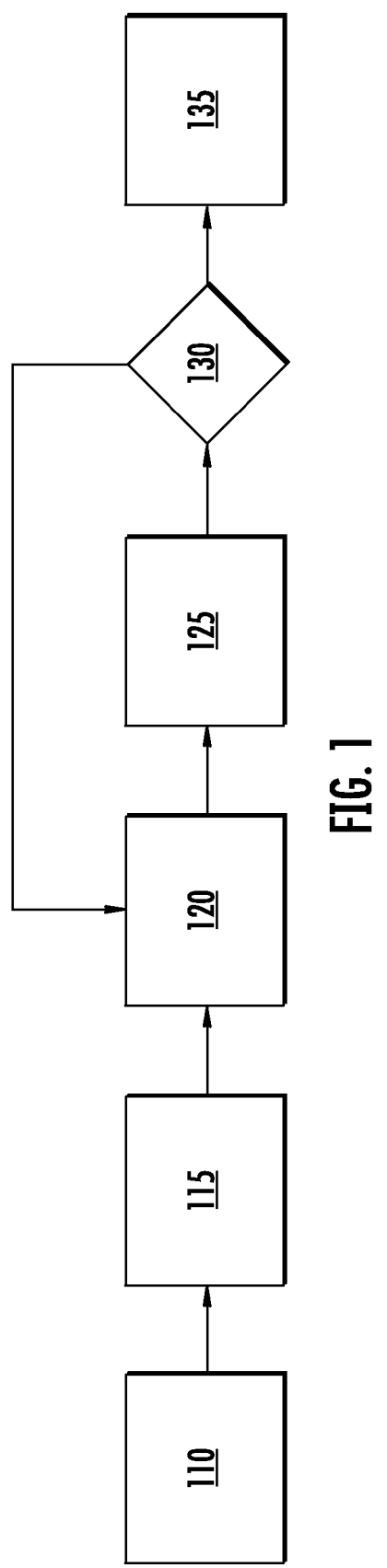
FIG. 1 depicts a block flow chart diagram graphically depicting an exemplary method.

An exemplary method is depicted in the flow chart shown in FIG. 1. As shown in FIG. 1, box 110 of the flow chart involves exposing a liquid comprising an ionic liquid and/or a low vapor-pressure organic solvent to a gaseous mixture at a first temperature and a first pressure until the liquid and the gaseous mixture are in equilibrium, thereby forming a liquid solution comprising the ionic liquid and/or low vapor pressure organic solvent and the compounds from the gas mixture. From there, the process flow moves to box 115, in which the liquid solution is isolated from the gaseous mixture, which can be accomplished by simply closing a valve between a container housing the liquid and a sample port connection to a low pressure line of a refrigerant heat transfer loop.

In box 120, the method determines a predicted vapor pressure function of the liquid solution at a second temperature as a function of the concentration of each of the subject compound and the at least one other identified compound or compounds. The predicted vapor pressure of the liquid solution at a given molar concentration of each of the compounds equals the sum of the vapor pressure of each compound multiplied by its given mole percentage based on total number of moles of the compounds from the gas mixture in solution in the liquid. The predicted vapor pressure function or curve can be modeled by first recognizing that ionic liquid and/or low vapor pressure organic solvent will have only a negligible contribution to the vapor pressure, and it can be assumed to be zero. The predicted vapor pressure at any given concentration can then be readily determined from known solubility profiles in the liquid for each of known identified compounds of the gas mixture. This can be illustrated by a simple example involving two gas compounds, R-32 and R-125, and an ionic liquid, 1-butyl-3-methylimidazolium hexafluorophosphate (BMIM/PF$_6$).

In this illustrative example, a gas mixture of R-32 and R-125 is sampled at 10° C. and 10 bar of pressure and brought into contact with the ionic liquid until it reaches equilibrium. A predicted vapor pressure function at 25° C. is modeled, for comparison to an actual measured vapor pressure at 25° C. This predicted vapor pressure can be modeled based on known and/or empirically determined data. Solubility data for these gas compounds in this ionic liquid are reported in the patent literature, for example, US 2007/0131535 A1, the disclosure of which is incorporated herein by reference in its entirety. A portion of this data is set forth in Table 1 below.

TABLE 1

| R125 mole fraction in R32/R125 sample | T = 10° C. | | | | | T = 25° C. | | | | |
|---|---|---|---|---|---|---|---|---|---|---|
| | | R125 | | R32 | | | R125 | | R32 | |
| | $P_{tot}$ (bar) | $P_i$ (bar) | mol. fraction in BMIM/PF$_6$ | $P_i$ (bar) | mol. fraction in BMIM/PF$_6$ | $P_{tot}$ (bar) | $P_i$ (bar) | mol. fraction in BMIM/PF$_6$ | $P_i$ (bar) | mol. fraction in BMIM/PF$_6$ |
| 0.1 | 10 | 1 | 0.044 | 9 | 0.849 | 17.6 | 1.7 | 0.044 | 15.9 | 0.849 |
| 0.2 | 10 | 2 | 0.081 | 8 | 0.768 | 16.7 | 3.1 | 0.081 | 13.6 | 0.768 |
| 0.3 | 10 | 3 | 0.122 | 7 | 0.685 | 15.9 | 4.4 | 0.122 | 11.5 | 0.685 |
| 0.4 | 10 | 4 | 0.173 | 6 | 0.599 | 15.4 | 5.9 | 0.173 | 9.5 | 0.599 |
| 0.5 | 10 | 5 | 0.243 | 5 | 0.509 | 15.4 | 7.7 | 0.243 | 7.7 | 0.509 |
| 0.6 | 10 | 6 | 0.340 | 4 | 0.417 | 15.8 | 9.8 | 0.340 | 6.0 | 0.417 |
| 0.7 | 10 | 7 | 0.470 | 3 | 0.321 | 16.4 | 12.0 | 0.470 | 4.4 | 0.321 |
| 0.8 | 10 | 8 | 0.643 | 2 | 0.221 | 17.4 | 14.5 | 0.643 | 2.9 | 0.221 |
| 0.9 | 10 | 9 | 0.865 | 1 | 0.117 | 19.9 | 18.4 | 0.865 | 1.5 | 0.117 |

Figure 2:
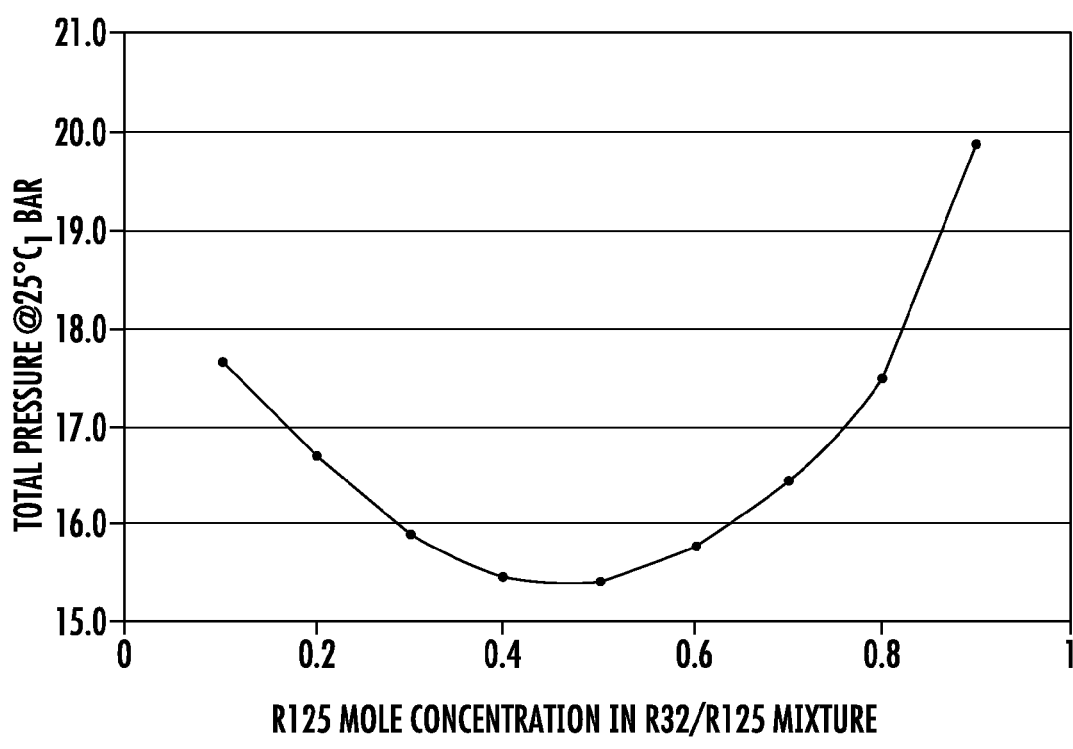
FIG. 2 is a plot of a predicted total vapor pressure function of an exemplary two-compound gas mixture dissolved in an ionic liquid as a function of mole fraction of one of the gas compounds.

Applying commercially-available curve fitting software to this data yields a higher order mathematical equation for the individual vapor pressures as a function of mole fraction for each compound, which can then be mathematically combined to produce a function of the total vapor pressure as a function of the mole fraction of the R-125, which is depicted for this illustrative example at 25° C. in the plot shown in FIG. 2.

Figure 3:
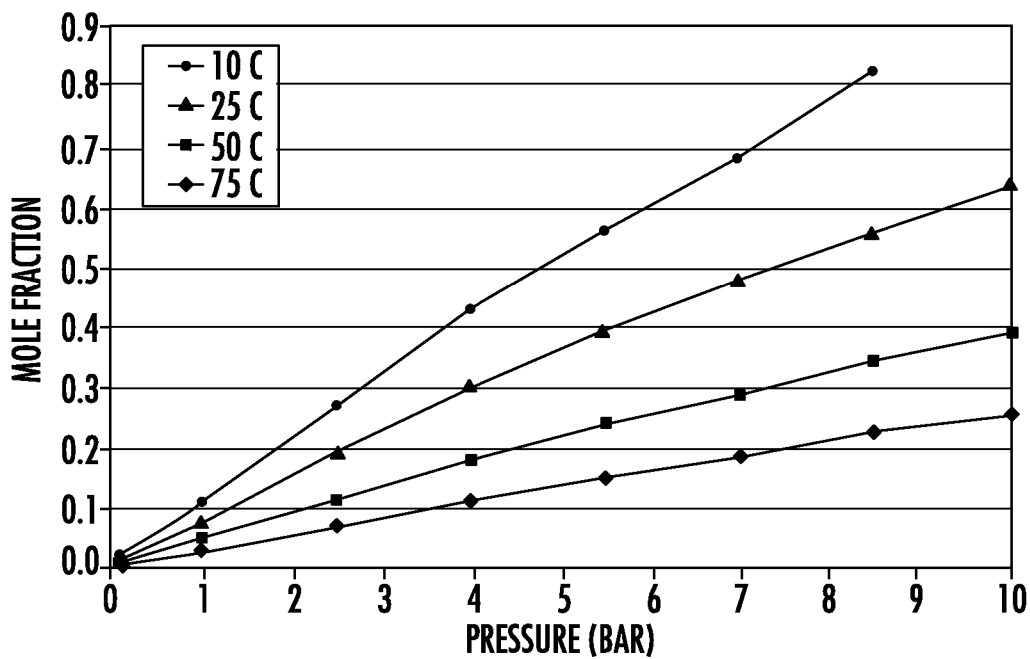
FIG. 3 is a plot of solubility of an exemplary gas compound showing mole fraction of the dissolved compound in solution versus vapor pressure at different temperatures.
Figure 4:
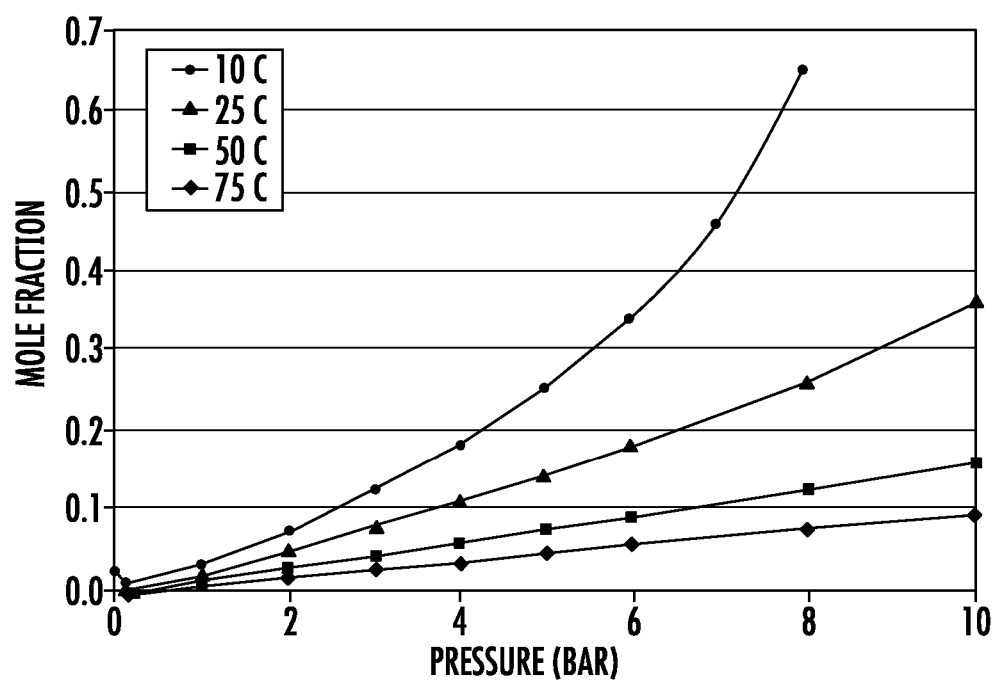
FIG. 4 is a plot of solubility of an exemplary gas compound showing mole fraction of the dissolved compound in solution versus vapor pressure at different temperatures.

Turning again now to FIG. 1, the process proceeds to box 125, in which the actual vapor pressure of the liquid solution at the second temperature is measured. In decision node 130, the actual measured vapor pressure is compared to the predicted vapor pressure function to see if a mole fraction for the compounds in the liquid solution can be determined. For the illustrative example, as can be seen in FIG. 2, throughout much of the realm covered by the figure, a given total vapor pressure can be produced by two different concentration profiles. For example, a total vapor pressure of 17 bar can be produced by a composition having an R-125 mole fraction of about 0.18 (and an R-32 mole fraction of about 0.82, or by a composition having an R-125 mole fraction of about 0.78 (and an R-32 mole fraction of about 0.22). In order to determine which concentration profile of the compounds has produced a particular measured vapor pressure, vapor pressure measurements at different temperatures can be utilized. Since the solubility profiles in the liquid are different for each of the compounds, and since they respond differently to temperature changes (see, e.g., the solubility plots for different temperatures shown in FIGS. 3 and 4 for R-32 and R-125, respectively, in BMIM/PF$_6$), a vapor pressure measurement at a different temperature than the second temperature will only be able to be produced by one of the two potential concentration profiles identified in box 120 in this illustrative example, which would be the actual concentration profile of the liquid solution. In practice, the higher order equation of FIG. 2 can be stored and utilized in a microprocessor to perform, or a series of data points from the plot of FIG. 2 can be stored in a look-up table as is known in the art.

In a two-component system like the illustrative R-125/R-32 system depicted here, the vapor pressure measurement at the different temperature can be the pressure and temperature at which the sample was taken, in this case a vapor pressure at 10 bar at 10° C. In more complex gas mixtures such as ternary or quaternary blends, vapor pressure measurements at third, fourth, or additional temperatures can be made as needed. As depicted in FIG. 1, if the result of the query in decision node 130 is that a concentration profile of the gas compounds dissolved in the liquid cannot be determined, then the process flow loops back to box 120 where a predicted vapor pressure function at a third temperature (or fourth or additional temperatures depending on the number of iterations of this logic loop) is determined in similar fashion as was the predicted vapor pressure function at the second temperature. This loop is repeated until the result of the query in decision node 130 is that a concentration profile of the gas compounds dissolved in the liquid can be determined.

If the liquid solution was maintained under conditions to keep all of the dissolved gas compounds from box 110 in solution (e.g., by maintaining the liquid in a fixed volume container with negligible vapor space), then the concentration profile determined in box 120 will be the same as the initial concentration profile produced in box 110. Although it is not required to keep all the gas compounds in solution, doing so greatly simplifies the mathematical modeling involved, as there is no need to account for quantities of gas compounds moving between a solution phase and a vapor phase at different temperature and pressure conditions, thereby changing the concentration profile of gas compounds dissolved in the liquid. The single concentration profile resulting from the logic loop of boxes 120, 125 and decision node 130 can be readily converted to the initial concentration of the gas compounds dissolved in the liquid produced by the sampling performed in box 110, which is either the same as the concentration profile determined in decision node 130 (in the case where the compounds have been maintained in solution throughout the process) or can be readily calculated.

The process flow then moves to box 135, where the partial vapor pressure is calculated for each of the gas compounds in the gaseous mixture. This is accomplished by dividing the mole percentage of each of the gas compounds in the concentration profile of gas compounds dissolved in the liquid resulting from box 110 by the solubility in the liquid at the first temperature of each compound, respectively. The mole percent of each compound in the gas mixture can then be calculated by dividing the partial vapor pressure of each compound by the total vapor pressure, which is the pressure of the gas mixture that was sampled in box 110 (10 bar in the case of the illustrative example described above).

Figure 5:
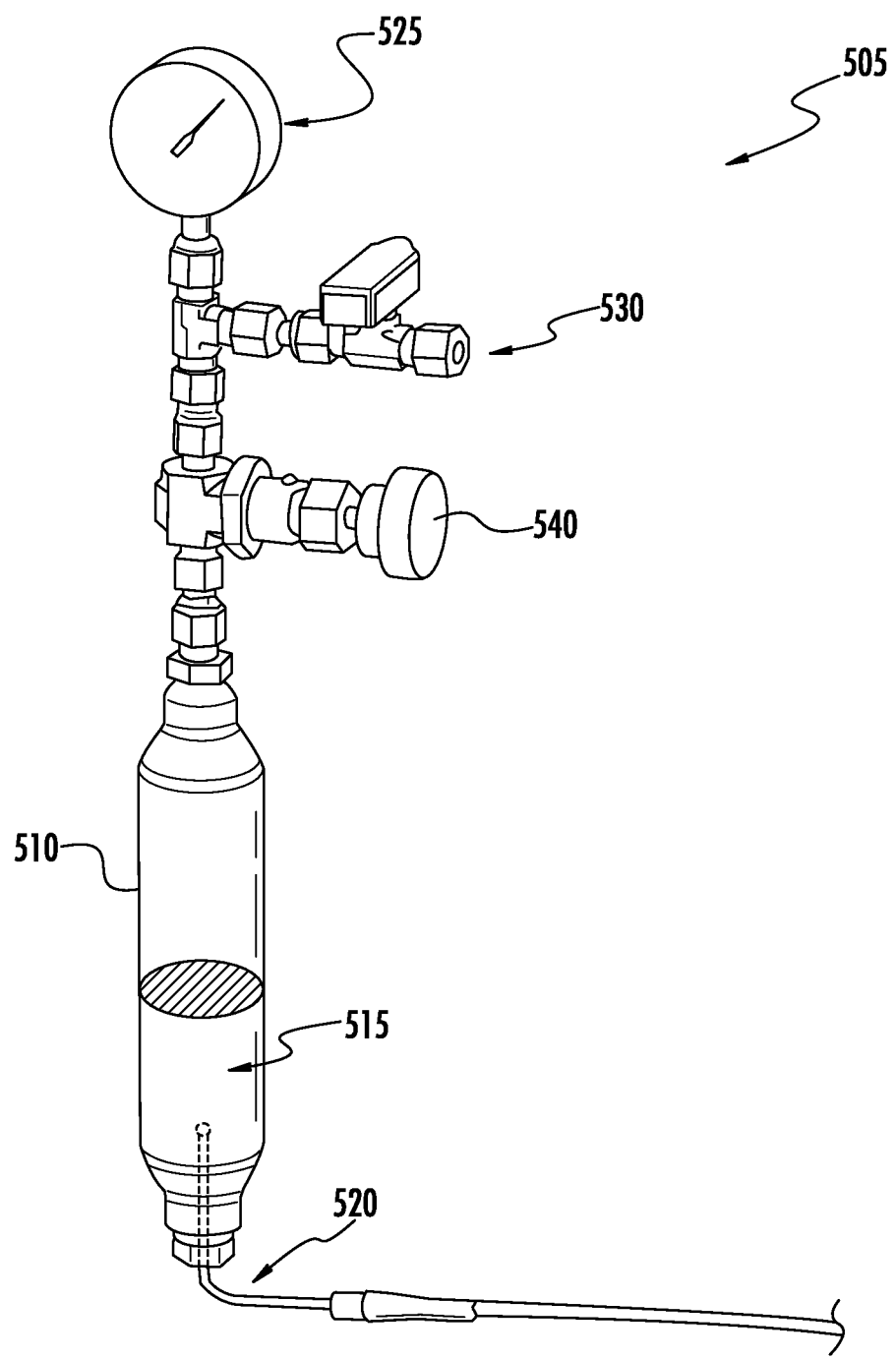
FIG. 5 depicts an exemplary apparatus as described herein.

Turning now to FIG. 5, an exemplary apparatus 505 is shown for carrying out the gas sampling and temperature and pressure measurements of the above-described method. The apparatus in FIG. 5 has a container 510 filled with an ionic liquid and/or low vapor pressure organic solvent 515. It is noted that although the container 510 is shown in FIG. 5 partially filled with the ionic liquid and/or low vapor pressure organic solvent 515 for purposes of illustration, in some embodiments as described above the container 510 is completely filled, leaving negligible vapor space. Temperature sensor 520 is disposed at the bottom of container 510, and pressure sensor 525 is disposed at the top. Sample port 530 is configured to connect to a corresponding sample port in a refrigerant circulation loop, and has valve 535 that can be opened for sampling and closed to isolate the liquid solution from the gas mixture after the two have reached equilibrium during the sampling process. Isolation valve 540 can be selectively opened during operation, and closed at other times such as to maintain a vacuum in container 510 when not in use.

An apparatus such as the one depicted in FIG. 5 can also include a controller (not shown) in communication with various components of the apparatus such as the temperature sensor 520 and the pressure sensor 525. The controller can be configured (i.e., can include software containing instructions) to perform various steps of the above-described process for determining concentrations of compounds in a gas mixture. The controller can also be in communication with components such as the valve 535, which communication can be direct (e.g., direct communication between the controller and an actuator for valve 535) or can be indirect (e.g., communication with a human apparatus operator through a communication interface such as a digital display, directing the operator to open or close the valve 535) in order to carry out steps such as isolating the liquid from the gas mixture after sampling.

In some embodiments, the above-described method steps are carried out in the order discussed hereinabove. However, some variations on ordering can be accommodated without adversely impacting performance. For example, it is not critical whether the pressure measurement at the second temperature is performed prior to or after determining a predicted vapor pressure function of the identified compounds in solution at that temperature. In some cases, the second temperature can be predetermined as the ambient temperature of the surroundings. In some embodiments, the second temperature or additional temperatures at which vapor pressure measurements will be taken can be determined by the controller based on availability of solubility data at certain temperatures or based on temperatures at which the solubility data indicates that pressure readings are likely to produce results that are readily combined with pressure measurements at other temperatures to eliminate the type of multiple solutions shown in FIG. 2.

Ionic liquids and low vapor pressure organic solvents contribute little or no vapor pressure of their own so that the vapor pressure measurements reflect the vapor pressure being produced by the gas compounds dissolved in the liquid and minimize the potential for contamination by vapor from the liquid transferring into the gas mixture being sampled.

Ionic liquids are well-known, and have been the subject of significant study and research. Ionic liquids tend to be air and water stable. Exemplary cations for ionic liquids used in the embodiments described herein include, but are not limited to imidazolium (e.g., 1-ethyl-3-methylimidazolium, 1-ethyl-2,3-dimethylimidazolium, 1-butyl-3-methylimidazolium ("BMI"), 1-hexyl-3-methyl-imidazolium ("HMI"), pyridinium (e.g., N-methylpyridinium), tetraalkylammonium, pyrrolidinium (e.g., 1-butyl-1-methyl-pyrrolidinium ("BMPyr"), trialkylsulfonium (e.g., triethylsulfonium), pyrazolium, triazolium, thiazolium, oxazolium, pyridazinium, pyrimidinium, pyrazinium. Exemplary anions for ionic liquids used in the embodiments described herein include, but are not limited to, tetrafluoroborate ($BF_4$), hexafluorophosphate ($PF_6$), trifluoromethanesulfonate ($CF_3SO_3$), trifluoroethanoate, nitrate, SCN, $HSO_4$, $HCO_3$, $CH_3SO_3$, $CH_3CH_2SO_4$, $(CH_3(CH_2)_3O)_2POO$, $(CF_3SO_2)_2N$, dicyanamide, $(CF_3CF_2SO_2)_2N$, L-(+)-lactate, $CH_3SO_4$, and $CH_3COO$, and the like.

In some exemplary embodiments, the ionic liquid has a cation that is an imidazolium, and more specifically the ionic liquid has the formula:

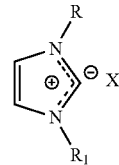

wherein, R and $R_1$ are independently selected from H, an unsubstituted or substituted alkyl group having 1 to 30 carbon atoms, or an unsubstituted or substituted aryl group having 6 to 30 carbon atoms. $X^\ominus$ is an anionic group, as described hereinabove, that associates with imidazolium to form an ionic-liquid cation/anion pair.

Low vapor pressure organic solvents are also well-known in the art. In some exemplary embodiments, the low vapor pressure organic solvent has a vapor pressure of less than 0.01 mmHg at 25° C. Examples of low vapor pressure organic solvents include mineral oil, polyolester oils, fatty alcohols, fatty acids, and hydrocarbon-based oils of up to 40 carbon atoms.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of measuring the concentration of an identified subject compound in a gaseous mixture comprising the subject compound and at least one other identified compound or compounds, comprising:

(a) exposing a liquid comprising an ionic liquid and/or a low vapor-pressure organic solvent to the gaseous mixture at a first temperature and a first pressure until the liquid and the gaseous mixture are in equilibrium, thereby forming a liquid solution comprising the ionic liquid and/or low vapor pressure organic solvent, the subject compound, and the at least one other compound or compounds;

(b) isolating the liquid solution from the gaseous mixture;

(c) determining a predicted vapor pressure function of the liquid solution at a second temperature as a function of the concentration of each of the subject compound and the at least one other identified compound or compounds, wherein the predicted vapor pressure of the liquid solution at a given molar concentration of each of the compounds equals the sum of the vapor pressure of each compound multiplied by its given mole percentage based on total number of moles of the subject compound and the at least one other identified compound or compounds in solution in the liquid;

(d) measuring the vapor pressure of the liquid solution at the second temperature;

(e) comparing the measured vapor pressure of the liquid solution at the second temperature with predicted vapor pressure function of the liquid solution at the second temperature and identifying all molar concentration profiles of the identified subject compound and the at least one other identified compound or compounds in the liquid for which the measured vapor pressure equals the predicted vapor pressure;

(f) if more than one molar concentration profile of the identified subject compound and the at least one other identified compound or compounds in the liquid provides a predicted vapor pressure that equals the measured vapor pressure at the second temperature, repeating steps (c)-(e) at different temperatures until a single molar concentration profile provides a predicted vapor pressure that matches the measured vapor pressure at each of the second and additional temperatures;

(g) converting the single concentration profile resulting from step (e) or step (f) by the solubility in the liquid at the first temperature of each of the identified subject compound and the at least one other identified compound or compounds, respectively to a concentration profile of the identified subject compound and the at least one other identified compound or compounds in the liquid resulting from step (a);

(h) calculating a partial vapor pressure for each of the identified subject compound and the at least one other identified compound or compounds in the gaseous mixture by dividing the mole percentage of each of the identified subject compound and the at least one other identified compound or compounds in; and (i) calculating a mole percent of the identified subject compound in the gaseous mixture by dividing the partial vapor pressure of the identified subject compound from step (h) by the sum of the partial vapor pressures for each of the identified subject compound and the at least one other identified compound or compounds from step (h).

2. The method of claim 1, further comprising calculating a mole percent for each of the at least one other identified compound or compounds by dividing the partial vapor pressure of each of the at least one other identified compound or compounds from step (g) by the sum of the partial vapor pressures for each of the identified subject compound and the at least one other identified compound or compounds from step (g).

3. The method of claim 1, wherein the liquid is isolated in step (b) in a container with negligible vapor space.

4. The method of claim 3, wherein the liquid is maintained in the container with negligible vapor space throughout steps (c)-(f) under temperature and pressure conditions to maintain in solution in the liquid all of the dissolved identified subject compound and all of the dissolved at least one other identified compound or compounds.

5. The method of claim 1, wherein the volume of the container is maintained constant throughout steps (c)-(f).

6. The method of claim 1, wherein the second temperature and each of said different temperatures are each higher than the first temperature.

7. The method of claim 1, wherein the liquid comprises an ionic liquid.

8. The method of claim 7, wherein the ionic liquid comprises one or more anions selected from the group consisting of Cl, Br, $BF_4$, $PF_6$, $AlCl_4$, SCN, $HSO_4$, $HCO_3$, $CH_3SO_3$, $CH_3CH_2SO_4$, $(CH_3(CH_2)_3O)_2POO$, $(CF_3SO_2)_2N$, dicyanamide, $CF_3SO_3$, $(CF_3CF_2SO_2)_2N$, L-(+)-lactate, $CH_3SO_4$, and $CH_3COO$.

9. The method of claim 7, wherein the ionic liquid comprises an imidazolium, pyridinium, tetralkylammonium, pyrrolidinium, trialkylsulfonium, pyrazolium, triazolium, thiazolium, oxazolium, pyridazinium, pyrimidinium, or pyrazinium cation.

10. The method of claim 7, wherein the ionic liquid comprises one or more cations according to the formula:

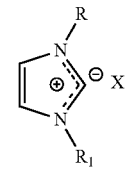

wherein
R and R1 are independently H, substituted or unsubstituted alkyl of 1 to 30 carbon atoms, or substituted or unsubstituted aryl of 6 to 30 carbon atoms; and
X is an anion.

11. The method of claim 10, wherein R is selected from the group consisting of $-(CH_2)_3CH_3$, $-CH_2CH_3$, $-CH_3$, $-CH=CH_2$, $-CH_2CN$, and $-(CH_2)_3CN$, and $R_1$ is selected from the group consisting of H, $-CH_3$, $-CH_2CN$, and $-(CH_2)_3CN$.

12. The method of claim 1, wherein the liquid comprises a low vapor pressure organic solvent.

13. The method of claim 12, wherein the low vapor pressure organic solvent has a vapor pressure of less than 0.01 mm Hg at 25° C.

14. The method of claim 1, wherein the gaseous mixture is a refrigerant blend in a heat transfer loop of a refrigeration system.

15. An apparatus for determining the concentration of an identified subject compound in a gaseous mixture comprising the subject compound and at least one other identified compound or compounds, comprising
a container having a liquid therein comprising an ionic liquid and/or a low vapor-pressure organic solvent;
a temperature sensor for measuring temperature of the liquid in the container;

a pressure sensor for measuring vapor pressure of the liquid;

a sample port in interruptible fluid communication with the interior of the container; and a controller configured to:

(a) open fluid communication between the sample port and the container when the sample port is connected the gaseous mixture to expose the liquid in the container to the gaseous mixture at a first temperature and a first pressure until the liquid and the gaseous mixture are in equilibrium, thereby forming a liquid solution comprising the ionic liquid and/or low vapor pressure organic solvent, the subject compound, and the at least one other compound or compounds;

(b) interrupt fluid communication between the sample port and the container to isolate the liquid solution from the gaseous mixture;

(c) determine a predicted vapor pressure function of the liquid solution at a second temperature, which can be the same as or different than the first temperature, as a function of the concentration of each of the subject compound and the at least one other identified compound or compounds, wherein the predicted vapor pressure of the liquid solution at a given molar concentration of each of the compounds equals the sum of the vapor pressure of each compound multiplied by its given mole percentage based on total number of moles of the subject compound and the at least one other identified compound or compounds in solution in the liquid;

(d) record a measured vapor pressure of the liquid solution sensed by the pressure sensor at the second temperature;

(e) compare the measured vapor pressure of the liquid solution at the second temperature with predicted vapor pressure function of the liquid solution at the second temperature and identifying all molar concentration profiles of the identified subject compound and the at least one other identified compound or compounds in the liquid for which the measured vapor pressure equals the predicted vapor pressure;

(f) if more than one molar concentration profile of the identified subject compound and the at least one other identified compound or compounds in the liquid provides a predicted vapor pressure that equals the measured vapor pressure at the second temperature, repeat steps (c)-(e) at different temperatures until a single molar concentration profile provides a predicted vapor pressure that matches the measured vapor pressure at each of the second and additional temperatures;

(g) convert the single concentration profile resulting from step (e) or step (f) by the solubility in the liquid at the first temperature of each of the identified subject compound and the at least one other identified compound or compounds, respectively to a concentration profile of the identified subject compound and the at least one other identified compound or compounds in the liquid resulting from step (a);

(h) calculate a partial vapor pressure for each of the identified subject compound and the at least one other identified compound or compounds in the gaseous mixture by dividing the mole percentage of each of the identified subject compound and the at least one other identified compound or compounds in; and (i) calculate a mole percent of the identified subject compound in the gaseous mixture by dividing the partial vapor pressure of the identified subject compound from step (h) by the sum of the partial vapor pressures for each of the identified subject compound and the at least one other identified compound or compounds from step (h).

16. The apparatus of claim 15, wherein the liquid fills the container, leaving negligible vapor space.

17. The apparatus of claim 15, wherein the liquid comprises an ionic liquid.

18. The apparatus of claim 15, wherein the liquid comprises a low vapor pressure organic solvent.

\* \* \* \* \*